United States Patent
Kreymann

(10) Patent No.: US 8,480,899 B2
(45) Date of Patent: Jul. 9, 2013

(54) MEANS FOR REMOVING PROTEIN-BOUND SUBSTANCES

(75) Inventor: Bernhard Kreymann, München (DE)

(73) Assignee: Hepa Wash GmbH, Garching (DE)

( * ) Notice: Subject to any disclaimer, the term of this patent is extended or adjusted under 35 U.S.C. 154(b) by 449 days.

(21) Appl. No.: 12/288,851

(22) Filed: Oct. 22, 2008

(65) Prior Publication Data

US 2009/0120876 A1    May 14, 2009

Related U.S. Application Data

(60) Division of application No. 10/980,276, filed on Nov. 4, 2004, now Pat. No. 7,455,771, which is a continuation of application No. PCT/EP03/04940, filed on May 12, 2003.

(30) Foreign Application Priority Data

May 14, 2002   (EP) .................... 02010185

(51) Int. Cl.
| | |
|---|---|
| *B01D 63/04* | (2006.01) |
| *B01D 61/26* | (2006.01) |
| *B01D 61/28* | (2006.01) |
| *B01D 61/32* | (2006.01) |
| *B01D 61/24* | (2006.01) |

(52) U.S. Cl.
USPC ...... 210/321.71; 210/645; 210/644; 210/648; 210/647; 210/175; 604/5.01; 604/6.08; 604/6.09

(58) Field of Classification Search
None
See application file for complete search history.

(56) References Cited

U.S. PATENT DOCUMENTS

| | | | |
|---|---|---|---|
| 4,375,414 | A | 3/1983 | Strahilevitz |
| 4,663,049 | A | 5/1987 | Kolff et al. |
| 5,744,042 | A | 4/1998 | Stange et al. |
| 6,264,680 | B1 | 7/2001 | Ash |
| 6,821,431 | B2 | 11/2004 | Collins et al. |
| 2002/0019603 | A1 | 2/2002 | Strahilevitz |
| 2002/0158019 | A1 | 10/2002 | Collins et al. |
| 2003/0105424 | A1* | 6/2003 | Karoor et al. ............ 604/29 |

FOREIGN PATENT DOCUMENTS

| | | |
|---|---|---|
| EP | 0 615 780 | 4/2001 |
| FR | 2 651 438 | 3/1991 |
| JP | 200072658 | 7/2007 |
| WO | WO 84/00689 | 3/1984 |
| WO | 9421363 | 9/1994 |
| WO | WO01/51185 | 7/2001 |

OTHER PUBLICATIONS

J. G. O'Grady et al, Liver, Pancreas, and Biliary Tract, "Controlled Trails of Charcoal Hemoperfusion and Prognostic Factors in Fulminant Hepatic Failure", Gastroenterology 94: pp. 1186-1192, 1988.

(Continued)

*Primary Examiner* — Krishnan S Menon
(74) *Attorney, Agent, or Firm* — Klauber & Jackson LLC

(57) ABSTRACT

The present invention relates to a means of dialysis for removing protein-bound substances from a biological fluid, especially blood or blood plasma, which contains at least one means for solubilizing protein-binding substances to be removed into the biological fluid and/or dialysis fluid, and to a process for removing protein-bound substances from a biological fluid.

19 Claims, 3 Drawing Sheets

OTHER PUBLICATIONS

Jan Stange et al., Artificial Organs, 26 (2), International Society for Artificial Organs, "The Molecular Adsorbents Recycling System as a Liver Support System Based on Albumin Dialysis: A Summary of Preclinical Investigations, Prospective, Randomized, Controlled Clinical Trail, and Clinical Experience from 19 Centers" pp. 103-110, 2002.

Case Report on Journal of Hepatology 1999.

Schwarzbeck, et al., Clin Nephrol, 1977 7(3):125-7.

* cited by examiner

MEANS FOR REMOVING PROTEIN-BOUND SUBSTANCES

This application is a division of U.S. Ser. No. 10/980,276 filed Nov. 4, 2004 which is a continuation of international application PCT/EP03/04940, filed on May 12, 2003, now U.S. Pat. No. 7,455,771.

The present invention relates to a means for removing protein-bound substances from a biological fluid, especially blood or blood plasma, which contains at least one means for changing the concentration ratio of toxin-protein complex to free toxin and free protein in the biological fluid and/or dialysis fluid, and to a process for removing protein-bound substances from a biological fluid. The term "toxin" is understood very broadly here and additionally covers all protein-bound substances which normally are not directly referred to as toxins, such as drugs, electrolytes, hormones, fats, vitamins, gases, and metabolic degradation products like bilirubin.

In a number of diseases, particularly including acute or chronic kidney failure, acute or chronic liver failure or exogenous intoxications, pathogenic substances dissolved in the plasma or bound to proteins must be removed from the blood. The conventional processes of haemodialysis, haemofiltration or haemodiafiltration only allow a small proportion of protein-bound substances to be eliminated.

The deficient elimination of protein-bound substances is currently only of secondary importance in renal function replacement. The life expectancy of patients with acute or chronic kidney failure can be normalized by a renal replacement therapy (with recovery of the organ function in the case of acute kidney failure) or at least prolonged for a number of years (in the case of patients still requiring a renal replacement therapy).

The situation is quite different for acute liver failure or an acute worsening of chronic liver failure. Methods comparable to renal replacement therapy are currently not available in this case.

The hepatic function can essentially be subdivided into two main functions:

the synthesis of vital proteins and the removal of mainly protein-bound toxins.

Basically only liver transplantation is currently available to replace the synthetic function. Although so-called bioreactors are known, with cells that at least partially take over the synthetic function of normal liver cells, these can only be used experimentally at the present time and their function is still insufficient. Liver transplantations are performed on approx. 20% of patients with acute liver failure because no adequate process for taking over the detoxication function exists, so the time taken for the hepatic function to recover cannot be bridged.

Protein-bound substances probably play an important role in the pathogenesis of hepatic encephalopathy, hepatic pruritus and hepatorenal syndrome. These pathogenic substances, which are bound predominantly to albumin, include especially aromatic compounds like phenol derivatives, indole derivatives, furan derivatives or aromatic amino acids, bilirubin, $C_4$-$C_7$ carboxylic acids, mercaptans, substances similar to digitoxin and benzodiazepine, and metal cations like copper cations, aluminium cations or iron cations. One of the most important diseases here is hepatic encephalopathy as it can be life-threatening and/or leave permanent damage.

Since the 70's there have been a variety of attempts, based largely on the dialysis technique, to replace the detoxication function of the liver:

1. Haemodialysis, Haemofiltration or Haemodiafiltration

These conventional processes are currently used on many patients with liver failure because in most cases, in the final stage of liver disease, a hepatorenal syndrome occurs which also leads to kidney failure that has to be treated by dialysis. However, these processes do not achieve a sufficient removal of protein-bound substances and essentially only eliminate water-soluble substances of low or intermediate molecular weight.

2. Haemoperfusion

In this process, blood or plasma is passed over an adsorber (charcoal and/or cation or anion exchanger) in order to remove the protein-bound toxins (O'Grady J.G., Gimson A.E., O'Brien C.J., Pucknell A., Hughes R.D., Williams R.: Controlled trials of charcoal hemoperfusion and prognostic factors in fulminant hepatic failure. Gastroenterology, 94, 1186-1192, 1988). This method has the disadvantage of being non-specific, so vital substances are also removed from the blood or plasma.

3. Albumin as Adsorber With Two Different Processes

A. MARS (Molecular Adsorbents Recirculating System)

The MARS described in EP 0 615 780 uses a special albumin-coated dialysis membrane. The recirculating albumin-containing dialysate is passed over 2 adsorber columns (charcoal and resin) in order to eliminate the protein-bound toxins removed from the patient by dialysis and to prepare the binding sites of the albumin in the dialysate for toxins (Stange J., Hassanein T.I., Mehta R., Mitzner S.R., Bartlett R.H.: The molecular adsorbents recycling system as a liver support system based on albumin dialysis: a summary of preclinical investigations, prospective, randomized, controlled clinical trial, and clinical experience from 19 centers. Artif. Organs, 26, 103-110, 2002).

B. Albumin Dialysis

Albumin dialysis is a process related to continuous haemodialysis. A feature of continuous renal replacement therapy is the use of slow dialysate flows (1-2 l/h compared with 30 l/h in normal dialysis). In albumin dialysis, in contrast to conventional continuous renal replacement therapy, albumin is added to the dialysate to give a 5% solution (Kreymann B., Seige M., Schweigart U., Kopp K.F., Classen M.: Albumin dialysis: effective removal of copper in a patient with fulminant Wilson disease and successful bridging to liver transplantation: a new possibility for the elimination of protein-bound toxins. J. Hepatol., 31, 1080-1085, 1999). The use of albumin is based on its being the main carrier protein for protein-bound toxins in the blood.

For use on large numbers of patients, all the albumin-based systems described above incur high treatment costs (current treatment costs for MARS or albumin dialysis are approx. 2500 euros/day). Furthermore, these systems offer an unsatisfactory detoxication efficiency: on average only an approx. 10-30% reduction in the bilirubin level as a marker for protein-bound substances. Although the albumin-based dialysis processes bring about an improvement in the symptoms of hepatic encephalopathy, a normalization of the values cannot be achieved as a consequence of the high treatment costs.

The object of the present invention is therefore to provide a means of dialysis and a dialysis process with which protein-bound substances, together with other unwanted dialysable substances, can be removed from a biological fluid in one step in a simple and cost-effective manner.

This object is achieved according to the invention by the means and the process described herein.

The object is achieved according to the invention by a process in which, with a suitable means, the concentration ratio of toxin-protein complex to free toxin and free protein in a dialysis fluid circuit, in a biological fluid circuit or in both circuits is shifted in favour of the free substances, and the free toxin is then removed. Analogously it is also possible to consider the concentration ratio of adsorbed toxin to free toxin and adsorbent.

This solution has the advantage that, because they have been solubilized, the substances can be removed easily and efficiently from the biological fluid.

Within the framework of the present invention, dissolved substances and free toxin are understood as meaning not only individual molecules solvated by the solvent, but also those bound to dialysable substances. Toxins bound to dialysable substances can also be dialysable as complexes.

This process not only affords a rapid dialysis, coupled with an appreciable cost advantage, but also makes it possible to achieve a particularly thorough purification of the biological fluid.

In the case of blood or blood plasma purification, this process further affords a more patient-friendly method of treatment which, in the area of emergency medicine, for acutely life-threatening conditions, can be of crucial importance for the success of the treatment.

The means for changing the concentration ratio of toxin-protein complex to free toxin and free protein comprises a device for adjusting the pH of the usable fluids, a device for adjusting the temperature of the usable fluids, a device for adding substituate to dilute or change the composition (for instance the salt content) of the usable fluids, a device for adding dialysable compounds binding to the substances to be removed, and a device for irradiating the usable fluids with waves. Within the framework of the present invention, the different devices can be combined with one another in any desired manner. It is preferable to use at least one device for adjusting the pH and at least one device for adjusting the temperature in a circulation system.

One advantage of the present invention is that, with simple means, i.e. conventional devices for adding solutions of acids, bases, substituate or dialysable substances, or conventional heating, cooling or ultrasonic apparatuses or other generators of light, infrared, ultraviolet or electromagnetic waves (hereafter referred to as waves), the substances to be removed can be solubilized in a simple and cost-effective manner by weakening the bond between the protein-binding substances and carrier proteins or adsorbers. The dissolved substances (toxins) are dialysable and hence easy to remove.

It has in fact been found that the binding affinity of carrier proteins like albumin or adsorbers for toxins can be selectively lowered by a number of measures, thereby increasing the concentration of the free toxins in the solution. The protein-bound substances in the biological fluid or dialysis fluid are actually in equilibrium with a small amount of non-bound substances. Lowering the binding affinity makes it possible to increase the concentration of the non-bound, dialysable substances, the free substances passing into solution.

These measures include raising the temperature of the fluid containing bound toxins, changing the pH (acidic and basic range), irradiating with waves, diluting the fluid, changing the salt content and introducing dialysable substances that bind to bind to the toxins. The last of these measures results in the formation of dialysable complexes.

If provision is made in the dialysis fluid circuit for at least one means according to the invention for changing the concentration ratio of toxin-protein complex to free toxin and free protein, the dialysis fluid which can be used in the means of dialysis should contain an adsorber for the substances to be removed from the biological fluid. A small proportion of the protein-binding toxins in the biological fluid is in the free form in solution and this proportion can diffuse through the semipermeable membrane in the dialyser and bind to the free binding sites of the adsorber in the dialysis fluid. Then, via a means according to the invention for changing the concentration ratio of toxin-protein complex to free toxin and free protein, for example a device for adding acid, the binding affinity between adsorber and toxin is at least temporarily lowered, whereby the substances to be removed pass into solution and can be removed from the dialysis circuit via dialysis (diffusion) or filtration (convection) or a combination of both processes, hereafter called diafiltration.

According to the invention, adsorber and free toxin can also be separated by centrifugation, as used e.g. in plasma separation for carrying out plasmapheresis. Within the framework of the present invention, centrifugation thus constitutes an alternative to dialysis as a separation method.

Provision for at least one means according to the invention for changing the concentration ratio of toxin-protein complex to free toxin and free protein can also be made in the circuit of the biological fluid containing substances to be removed, bound to a carrier protein. Thus, for example, the effect of increasing the temperature is to lower the binding affinity of the carrier protein and solubilize the substances, enabling the dissolved, free substances to be dialysed.

Preferably, both the biological fluid circuit and the dialysis fluid circuit contain at least one means according to the invention for changing the concentration ratio of toxin-protein complex to free toxin and free protein.

One advantage of the invention is that substances with different binding behaviour can be removed by the various means available, especially if different measures are combined with one another.

One particularly efficient and cost-effective means is the device for adjusting the pH of the fluids. Adjusting the pH of the fluids to the acidic and/or basic range makes it possible selectively to influence the binding of different substances to the carrier proteins or adsorbers. Thus, adding an acid makes it possible to lower the pH of the fluid, thereby reducing the binding of certain toxins to proteins in the acidic range and hence increasing the concentration of free toxins in the fluid.

For example, the binding of copper ions to albumin can be weakened in this way so that free, dissolved copper ions in the following filter can be removed by dialysis, filtration, diafiltration or centrifugation. Analogously, the pH of the fluid can be adjusted to the basic range so that the toxins liberated in the alkaline range can then be eliminated from the fluid by dialysis, filtration or diafiltration.

Analogously, by adding a base, it is possible to weaken the binding of certain toxins to proteins and hence increase the concentration of free toxin in the fluid, a pH range of 8-13 being preferred in this case.

After removal of the toxins from the fluid by means of dialysis, filtration, diafiltration or centrifugation, the pH is optionally adjusted to a different advantageous value.

This can be of advantage particularly when working with an adsorber, e.g. albumin. A different advantageous pH is then chosen so that the affinity of the adsorber for the toxin is increased again. This allows recycling of the adsorber and hence offers a decisive cost advantage.

A circulation system (for dialysis fluid or biological fluid to be purified) contains preferably two and very particularly preferably three devices for adjusting the pH, so that the pH can be adjusted to the acidic or basic range with the first device, to the basic or acidic range, respectively, with the second device and back to the original range (usually neutral) with the third device. As a further preference, a circulation system (for dialysis fluid or biological fluid to be purified) contains two devices for adjusting the temperature so that the usable fluid can for example be heated and then brought back to the previous temperature, or to another desired temperature, by cooling. Very particularly preferably, a circulation system contains three devices for adjusting the pH and two devices for adjusting the temperature.

Another advantage of the invention is that, by means of dialysis, filtration or diafiltration devices provided in the dialysis fluid circuit and/or biological fluid circuit, the dissolved, dialysable substances can be removed from the fluids (dialysis fluid or biological fluid to be purified) easily and efficiently after separation from the carrier proteins or adsorbers. This can be done using conventional dialysis apparatuses such as the ones known to those skilled in the art. In addition, it is preferable to use devices for changing the pH/temperature values and devices for appropriate monitoring of these changes. Advantageously, in the means according to the invention, a dialysis, filtration, diafiltration or centrifugation device is inserted downstream from a device for adjusting the pH/temperature of the fluid to be used, in order to remove the free, dissolved substances directly from the fluid. A particularly preferred means is one in which a device for adding acid or base, a dialysis, diafiltration, filtration or centrifugation device, a device for adding base or acid, a dialysis, filtration, diafiltration or centrifugation device and a device for adding acid or base are provided, in that order, in the dialysis fluid circuit and/or biological fluid circuit. This makes it possible to remove different protein-binding substances from the dialysis fluid and biological fluid very efficiently and the purified dialysis fluid can in turn be recycled to the dialyser to recharge the adsorber with protein-binding substances.

An advantage of one particular embodiment of the present invention, where a means for changing the concentration ratio of toxin-protein complex to free toxin and free protein, for example a device for adjusting the pH, is arranged only in the biological fluid circuit, is that, to remove unwanted protein-bound toxins, the dialysis fluid does not necessarily have to contain an adsorber, for example the acceptor protein albumin, which drastically reduces the dialysis costs.

Devices for adjusting the pH include especially devices for adding acid or base, for example metering pumps. Appropriate acids or bases are aqueous solutions of biologically compatible acids or bases. It is generally preferable to use acids or bases whose conjugate bases or acids are ions that occur naturally in the human organism. Examples of acids which can be used are hydrochloric acid, sulfuric acid or acetic acid, hydrochloric acid being preferred. Examples of bases which can be used are sodium hydroxide solution or potassium hydroxide solution, sodium hydroxide solution being preferred. The biological or dialysis fluid can be adjusted e.g. to a pH of between 1 and 7, advantageously of between 2.5 and 5, by adding acid, and to a pH of between 7 and 13, advantageously of between 8 and 13, by adding base. In each particular case the desired pH depends substantially on the nature of the fluid used, the nature of the protein and the properties of the substances to be removed. For example, the binding affinity of copper for albumin is significantly lowered in the pH range around two. Conversely, this means that copper has a particularly high binding affinity for albumin at a pH above about 3. It has also been observed, for example, that the binding affinity of bilirubin for albumin is significantly lowered at a pH of about 12.

Devices for adjusting the temperature include especially heating devices such as conventional heating apparatuses, microwave apparatuses or infrared apparatuses, or cooling devices such as conventional cooling units. One or more heating/cooling devices can be arranged in the dialysis fluid circuit and/or biological fluid circuit. In particular, the substances to be removed can be solubilized by heating or cooling the usable fluids, while the biological fluid or dialysis fluid can be brought back to the desired temperature by cooling or heating. The nature and extent of the temperature gradient used depends on the nature of the fluid, the adsorber and the toxin to be removed. For example, it is possible to heat first and then cool again. The reverse process may also be advantageous. It may also be advantageous to carry out the heating/cooling stepwise.

Another advantage of the invention is that the binding affinity of the adsorber can be selectively increased by a device for cooling or heating the usable dialysis fluid, whereby free, dissolved substances that have diffused into the dialysis fluid can be bound by recycled adsorbers.

The desired temperature of the fluids to be used is substantially dependent on their nature. If the biological fluid used is blood or partial blood products like blood plasma or fractions thereof, it is possible to heat to a temperature of up to approx. 150° C. (coupled with a corresponding pressure increase, e.g. as used in the heat sterilization of milk), preferably of up to 45° C. Thus heating beyond the physiological range is also possible. When using the means of dialysis according to the invention in an extracorporeal circuit on a patient, the temperature can be lowered again to an optimum value for the patient in the range from 35 to 37° C., or approx. 35° Celsius in is the case of patients with hepatic encephalopathy.

If the device for adjusting the temperature is used in the dialysis fluid circuit, the temperature can also be increased to over 150° C. according to the addition e.g. of steam, or a pressure increase, or other stabilizers (known from the pasteurization treatment of albumin).

The heating of the fluid to be used, in the circulation system, can be effected via direct heating of the fluid-filled tubing system by means of a heating apparatus or by means of irradiation with microwaves or infrared. It may be sufficient e.g. to have heating devices only in the dialysis fluid circuit, the biological fluid nevertheless being heated as well because of the heat exchange between the fluid to be purified and the dialysis fluid in the dialyser. In another embodiment, upstream from the entrance to the dialysis fluid circuit or biological fluid circuit, a heating device can also be inserted downstream from a device for adjusting the pH or a device for adding substituate. In this case the dialysis fluid and/or the fluid to be purified are heated by adding warm solutions.

An ultrasonic apparatus, for example, can be used as the device for irradiating with waves. Other appropriate devices are those suitable for generating light waves, ultraviolet waves, infrared waves, radio waves and microwaves.

Another possible means for changing the concentration ratio of toxin-protein complex to free toxin and free protein is a device for adding dialysable compounds binding to the substances to be removed. Said means can be conventional metering pumps which introduce aqueous solutions of the dialysable compounds. The dialysable substances, some of which are bound to toxins, can easily be removed via the conventional dialysis or diafiltration devices. Binding compounds which can be used are dialysable compounds of low/intermediate molecular weight that are distinguished by a strong affinity for the substances to be removed. The preferred compounds include caffeine, which binds to bilirubin, and common chelating agents like penicillamine, trientine, deferoxamine, preferiprone, HBED, vitamin C, BAL, DMPS or DMSA, which bind to metal cations such as copper ions or iron ions. The dialysable compounds can be added both to the biological fluid and to the dialysis fluid, but preferably to the dialysis fluid in order to avoid complications due to possible contamination of the biological fluid in the event of incomplete removal by dialysis.

Furthermore, synergistic effects can also occur when using two means for changing the concentration ratio of toxin-protein complex to free toxin and free protein, for example an increase in pH and the addition of a binding compound (e.g. caffeine).

Devices for adding substitute to dilute or change the salt content of the usable fluids include conventional metering pumps with which a substitute solution can be added. Such a device is preferably used in combination with a heating device, inserted downstream therefrom, so that warm substituate is added to the circuit of the fluids used. Suitable substituate solutions are aqueous solutions which can contain various salts as well as urea. These solutions can be commercial dialysis fluids which, as required, can be adjusted to the desired concentration by adding salts. However, as mentioned above, it is also possible to use stabilizers, agents for thinning the blood, such as heparin or citrate, or substances for changing the osmotic equilibrium, such as salts, or for changing the electrophysiological equilibrium (Donnan effect), such as negatively or positively charged substances. The substitute serves not only to solubilize the substances to be removed by changing the salt concentration in the fluid. The salt concentration of the biological fluid, e.g. blood, can also be precisely adjusted according to the patient's condition by adding substituate. Moreover, it can also be used to restore the binding capacity of recycled adsorber for toxins in the dialysis circuit. Also, the addition of urea may be necessary to improve the binding capacity of the adsorber.

The dialysers used can be conventional dialysers currently used e.g. for haemodialysis. It is also conceivable, however, to consider membranes with larger pores than those presently used for dialysis. The dialyser is equipped with a conventional semipermeable dialysis membrane; the diffusion through the membrane can optionally be supported by convective transport by means of filtration. The dialyser essentially comprises two chambers separated by a dialysis membrane, to each of which is connected a circulation system (tubing system) for the fluids to be used. The biological fluid to be purified and the dialysis fluid are conventionally conveyed in counter-current, but they can also be conveyed in co-current. Conventional components of a dialyser, such as manometers, air detectors, pumping devices like heparin pumps, blood pumps, etc., form part of the means according to the invention. The means according to the invention can achieve both slow dialysate flows (1-2 l/h) and normal dialysate flows (25-50 l/h) as well as intermediate rates, as required.

The biological fluids which can be used in the means according to the invention or in the process according to the invention include all human or animal body fluids, especially blood or blood plasma, particularly preferably of human origin. The removal of protein-bound substances from the biological fluids used is simultaneously accompanied by the elimination of water-soluble substances, for example urea or various ions, that can normally be removed in conventional dialysis. The protein-binding substances to be removed are preferably bound to the carrier protein albumin. The means according to the invention is particularly suitable for purifying blood and plasma in the medical sector and can be used both in the field of blood bank processing and for extracorporeal dialysis on patients.

The dialysis fluids used can be conventional dialysis fluids such as the ones known to those skilled in the art. The ion concentration can be adapted to the individual patient's needs. Customary ion-containing aqueous solutions or pure water can be used, as required. The conventional dialysis fluids are optionally provided with an adsorber for the protein-binding substances to be removed. Examples of possible adsorbers are resinate and acceptor proteins. A preferred acceptor protein is albumin, which can be human serum albumin, animal albumin or genetically engineered albumin. It is particularly preferable to use human serum albumin. The serum albumin solutions can optionally be diluted with water, conventional dialysis fluids or other fluids. The dialysis fluid used can contain human serum albumin in a concentration of 0.1 to 25 g per 100 ml, preferably of 2 to 10 g per 100 ml and particularly preferably of 4 to 6 g per 100 ml.

Other dialysis fluids which can be used are blood, blood serum or fresh frozen plasma. The dialysis fluid can also be dialysate from the bioreactor. Enormous quantities of blood are currently needed for bioreactors (systems working with living liver cells for hepatic replacement therapy); thus, up to one liter of blood has to be withdrawn from the patient's circulation during the circulation of the bioreactor. To stimulate the synthetic function of the liver cells in the bioreactor, however, it may also be sufficient to employ a system which uses a dialysate containing toxic substances that are normally removed in the liver. Accordingly, a dialysate as described under 1 and 2 can first be passed through the bioreactor in the extracorporeal circuit. This dialysate is then purified as described under 2 and the dialysate returned to the patient. To do this it may be necessary to add albumin continuously to the dialysate or to use a capillary or a membrane that is more permeable to albumin than dialysis filters used at the present time.

The means according to the invention can be equipped with one or more conventional pH meters and/or thermometers for monitoring the corresponding properties of the fluids used.

The invention further relates to a process for removing unwanted substances from a biological fluid, comprising the dialysis of a biological fluid against a dialysis fluid through a semipermeable membrane, characterized in that the dialysis fluid contains an adsorber for protein-binding substances to be removed, and in that the dialysis fluid is adjusted, by adding acid, base or dialysable substances, by dilution, by changing the salt content, by irradiation with waves or by heating, in such a way that the binding affinity of the adsorber for the bound substances is at least temporarily lowered, thereby increasing the concentration of the free unwanted substances in the dialysis fluid.

Provision is also made for a process for removing unwanted substances from a biological fluid, comprising the dialysis of a biological fluid against a dialysis fluid through a semipermeable membrane, characterized in that the biological fluid is adjusted, by adding acid, base or dialysable substances, by dilution, by changing the salt content, by irradiation with waves or by heating, in such a way that the binding affinity of the carrier protein for the bound substances to be removed is lowered, thereby increasing the concentration of the free unwanted substances in the biological fluid.

Also advantageous is a process using a circulation system which comprises an at least two-fold addition of acid, base or dialysable substances, dilution, changing of the salt content, irradiation with waves or heating/cooling of the dialysis fluid or biological fluid.

The processes and means according to the invention can be used in general for purifying biological fluids. Biological fluids include all human or animal body fluids, especially blood or blood plasma, particularly preferably of human origin. It is possible here to return the withdrawn fluids, especially blood or blood plasma, to the body or make them available for other purposes. Thus, for example, blood bottles can be purified or the purified biological fluids are made available for other commercial purposes or research purposes.

The means described above is suitable for carrying out the processes according to the invention. Further details, features and advantages of the process can be found in the above discussion of the means and in the Claims.

Three Examples of the invention are illustrated in greater detail below with reference to the Figures. The Figures are diagrammatic representations of particular embodiments of the means according to the invention.

FIG. 1 shows a means of haemodialysis consisting essentially of a dialyser (1), a dialysis fluid circuit (2) (only suggested in the Figure: used dialysate does not have to be recycled in this embodiment), a blood circuit (3) (only suggested in the Figure), heating and cooling apparatuses (6), a device (7) for adding substituate and a thermometer (10).

Figure 1:
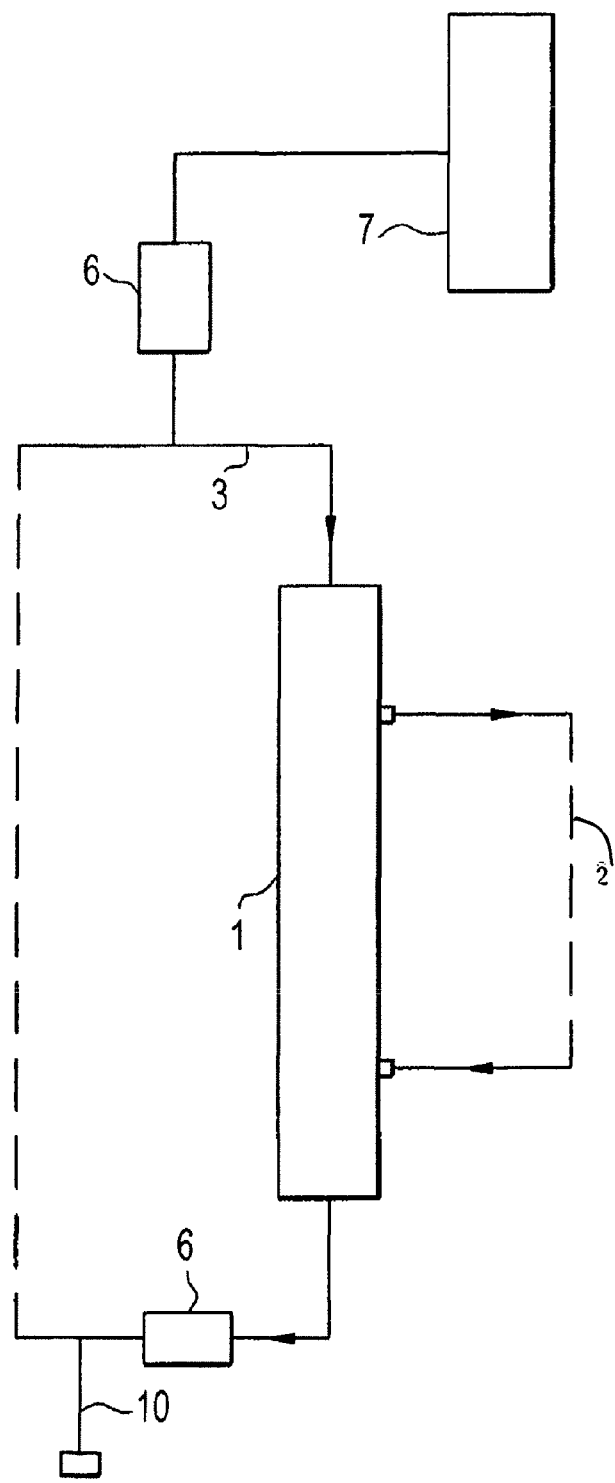
FIG. 1 is a simplified diagrammatic representation of an embodiment of the means according to the invention with heating and cooling devices and a device for adding substituate in the extracorporeal circuit.

Via the device (7), substituate, e.g. from conventional haemo-filtration solution, heated in the heating apparatus (6), is added to the blood in the blood circuit (3) before it enters the dialyser (1). The warm blood then enters the blood chamber of the dialyser (1). Because the temperature of the blood has been raised, there is an increased liberation of protein-bound substances from the carrier proteins, thus producing an increased pool of dissolved, dialysable toxins which diffuse through the dialysis membrane into the dialysis chamber of the dialyser (1). When the blood, purified of protein-bound substances, has left the dialyser (1), it is cooled again by the cooling unit (6) to a physiologically acceptable temperature, which is checked by the thermometer (10). Alternatively, the blood temperature and hence the patient's temperature can also be adjusted by controlling the dialysate temperature. The blood is then returned to the blood circuit (3).

Figure 2:
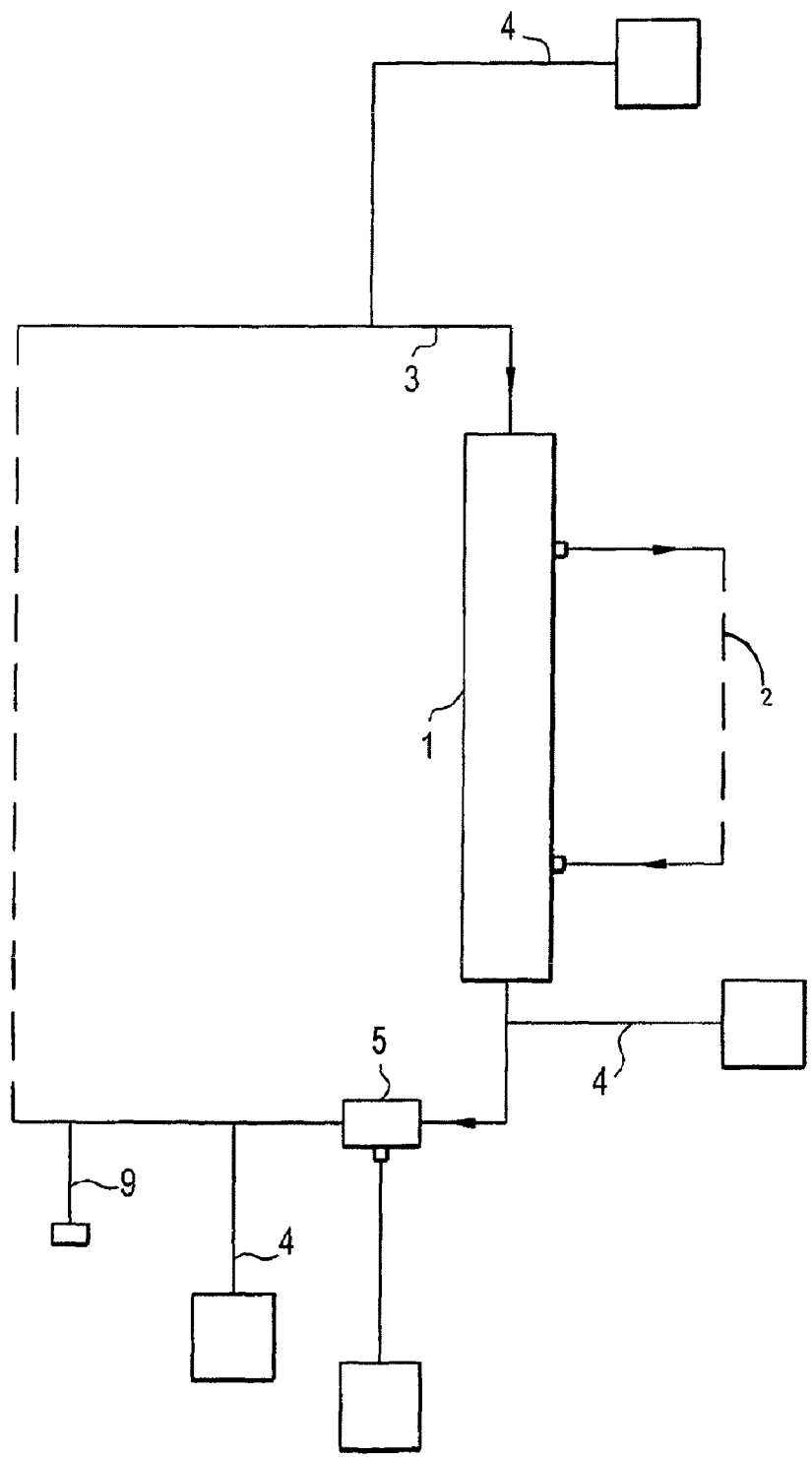
FIG. 2 is a simplified diagrammatic representation of an embodiment of the means according to the invention with devices for adjusting the pH in the extracorporeal circuit.

FIG. 2 shows a means of haemodialysis consisting essentially of a dialyser (1), a dialysis fluid circuit (2) (only suggested in the Figure: used dialysate does not have to be recycled in this embodiment), a blood circuit (3) (only suggested in the Figure), metering pumps (4) for adding acid or base, a dialyser (5) and a pH meter (11). By means of the metering pump (4), HCl solution is added to the blood in the blood circuit (3) before it enters the dialyser (1). This lowers the pH of the blood and some of the toxins pass into solution. The acidified blood then enters the blood chamber of the dialyser (1). The dissolved, dialysable substances can diffuse through the dialysis membrane into the dialysis chamber of the dialyser (1). When the blood, partially freed of protein-bound substances, has left the dialyser (1), NaOH solution is added by means of the metering pump (4), whereby the pH is adjusted to the basic range and further protein-binding toxins pass into solution. Downstream the blood enters another dialyser (5), where another dialysis, filtration or diafiltration is carried out in order to eliminate otherwise protein-bound substances dissolved in the alkaline range. The pH is then adjusted to approx. 7.4 in the neutral range with HCl solution via a metering pump (4), this being checked by the pH meter (11). The blood is then returned to the blood circuit (3).

Figure 3:
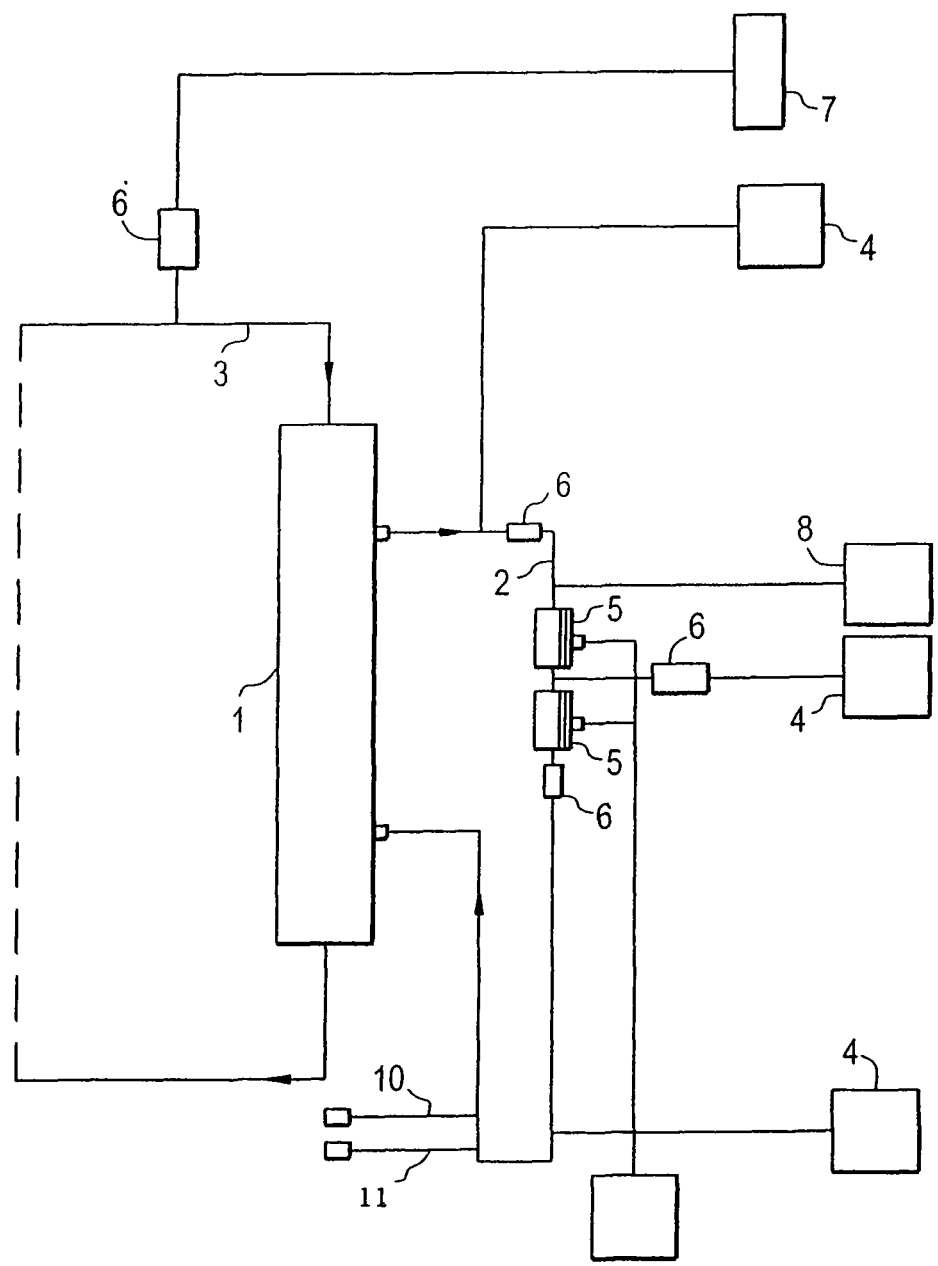
FIG. 3 is a simplified diagrammatic representation of an embodiment of the means according to the invention with heating and cooling devices, devices for adjusting the pH and a device for adding substituate in the dialysis fluid circuit.

FIG. 3 shows a means of haemodialysis consisting essentially of a dialyser (1), a dialysis fluid circuit (2), a blood circuit (3) (only suggested in the Figure), metering pumps (4) for adding acid or base, dialysers (5), heating and cooling apparatuses (6), a device (7) for adding substituate, a device (8) for adding caffeine, a pH meter (11) and a thermometer (10).

Via the device (7), substituate, e.g. from haemofiltration solution, heated in the heating apparatus (6), is added to the blood in the blood circuit (3) before it enters the dialyser (1). The warm blood then enters the blood chamber of the dialyser (1). Because the temperature of the blood has been raised, there is an increased pool of free, dialysable toxins which diffuse through the dialysis membrane into the dialysis chamber of the dialyser (1). The dialysis fluid also contains albumin, which binds to the toxins, so the pool of free substances in the dialysis fluid is kept low, thereby enhancing the diffusion of the toxins into the dialysis fluid. When the blood, purified of protein-bound substances, has left the dialyser (1), it is returned to the blood circuit (3).

The dialysis fluid from the dialyser (1), containing albumin-bound toxins, enters the dialysis fluid circuit (2). HCl solution is added to the dialysis fluid via the metering pump (4). This lowers the pH of the dialysis fluid and the pool of dissolved, free toxins in the fluid increases. Arranged downstream in the dialysis fluid circuit (2) is a heating apparatus (6) which heats the dialysis fluid to 41-45° C., whereby the pool of free toxins is increased further and the proportion of protein-bound toxins falls. The next component in the circulation system (2) is a caffeine metering pump (8). The addition of caffeine binds bilirubin in particular, thereby reducing the proportion of protein-bound bilirubin in the dialysis fluid. Downstream the dialysis fluid enters a dialyser (5), where some of the dialysis fluid is withdrawn from the system in order to keep the concentration of the adsorber in the desired range. In addition, the dialysate is purified by dialysis, filtration or diafiltration, especially to remove free, protein-binding substances and caffeine-bound bilirubin. The albumin cannot pass through the filter due to its high molecular weight. Arranged downstream from the exit from the dialyser (5) in the dialysis fluid circuit (2) is a metering pump (4) for adding NaOH solution, a heating apparatus (6) being arranged upstream from the entrance to the circuit. Downstream there follows another dialyser (5), which withdraws the added fluid from the system and eliminates substances dissolved in the alkaline range by dialysis, filtration or diafiltration. The next component in the circulation system (2) is a cooling device (6) by means of which the temperature of the dialysis fluid can be adapted according to the desired temperature of the patient. The following metering pump (4) is used to add HCl solution to the dialysis fluid in order to adjust its pH to the neutral range, so the binding capacity of albumin is increased again and the pH of the blood does not have an adverse influence in the dialyser. The next components in the circulation system (2) are a pH meter (11) and a thermometer (10) for checking the pH and temperature of the purified dialysis fluid before it reenters the dialyser (1).

The invention claimed is:

1. A method for dialysis of a biological fluid containing at least one protein-binding substance to be removed, comprising the following steps:

(a) passing the biological fluid through a first chamber of a first dialyser wherein the first chamber forms part of a biological fluid circuit, (b) passing a dialysis fluid containing a substance that functions as an adsorber for the substances to be removed from the biological fluid through a second chamber of the first dialyser wherein the second chamber forms part of a dialysis fluid circuit (c) at least partially solubilizing the protein binding substances to be removed in the dialysis fluid by adjusting the pH of the dialysis fluid to 8-13, and (d) passing the dialysis fluid with the pH adjusted to 8-13 through a second dialyser forming part of the dialysis fluid circuit.

2. The method according to claim 1, wherein the pH of the dialysis fluid is adjusted by adding base.

3. The method according to claim 1 further comprising heating or cooling the dialysis fluid.

4. The method according to claim 3, wherein heating is performed by a heating apparatus, a microwave apparatus or an infrared apparatus.

5. The method according to claim 3 wherein the cooling is performed by a cooling unit.

6. The method according to claim 1 further comprising passing the dialysis fluid through at least one additional dialyser in the dialysis fluid circuit.

7. The method according to claim 3 wherein the dialysis fluid is heated to 41-45° C.

8. The method according to claim 1 wherein the adsorber comprises albumin.

9. The method according to claim 1, wherein the dialysis fluid contains human serum albumin in a concentration of 1 to 25 g per 100 ml.

10. The method according to claim 1 further comprising adding a substituate to dilute or change the salt content of the dialysis fluid.

11. The method according to claim 1 further comprising recirculating the dialysis fluid.

12. The method according to claim 1 wherein the second dialyser is a filter.

13. The method according to claim 1, wherein the pH of the dialysis fluid is adjusted to 8-13 upstream of the second dialyser and the pH of the dialysis fluid is adjusted to 2.5-5.0 downstream of the second dialyser.

14. The method according to claim 6 wherein the pH of the dialysis fluid is adjusted to 2.5-5.0 upstream of the at least one additional dialyser in the dialysis fluid circuit.

15. The method according to claim 14 wherein the pH of the dialysis fluid is adjusted to 2.5-5.0 by adding acid.

16. The method according to claim 1 further comprising (e) adjusting the pH of the dialysis fluid to substantially neutral.

17. The method according to claim 1 further comprising providing a means for adjusting the pH of the dialysis fluid to substantially neutral.

18. A method for dialysis of a biological fluid containing at least one protein-binding substance to be removed, comprising the following steps:

(a) passing the biological fluid through a first chamber of a first dialyser wherein the first chamber forms part of a biological fluid circuit, (b) passing a dialysis fluid containing a substance that functions as an adsorber for the substances to be removed from the biological fluid through a second chamber of the first dialyser wherein the second chamber forms part of a dialysis fluid circuit (c) at least partially solubilizing the protein binding substances to be removed in the dialysis fluid by adjusting the pH of the dialysis fluid to 8-13, (d) passing the dialysis fluid with the pH adjusted to 8-13 through a second dialyser forming part of the dialysis fluid circuit, and (e) adjusting the pH of the dialysis fluid to essentially neutral.

19. The method according to claim 18 further comprising heating or cooling the dialysis fluid.

* * * * *